(12) United States Patent
Huang

(10) Patent No.: US 10,478,516 B1
(45) Date of Patent: Nov. 19, 2019

(54) SEALED CONTAINER STRUCTURE

(71) Applicant: Aromate Industries Co., Ltd., New Taipei (TW)

(72) Inventor: Chi-Chuan Huang, New Taipei (TW)

(73) Assignee: AROMATE INDUSTRIES CO., LTD., New Taipei (TW)

( * ) Notice: Subject to any disclaimer, the term of this patent is extended or adjusted under 35 U.S.C. 154(b) by 44 days.

(21) Appl. No.: 15/990,722

(22) Filed: May 28, 2018

(51) Int. Cl.
*A61L 9/12* (2006.01)
*B65D 75/58* (2006.01)
*A61L 9/04* (2006.01)
*A61L 9/03* (2006.01)
*A01M 1/20* (2006.01)

(52) U.S. Cl.
CPC .............. *A61L 9/12* (2013.01); *A01M 1/2055* (2013.01); *A61L 9/03* (2013.01); *A61L 9/04* (2013.01); *B65D 75/5855* (2013.01); *A61L 2209/13* (2013.01)

(58) Field of Classification Search
CPC ..... A61L 9/03; A61L 9/04; A61L 9/12; A61L 2209/13; A01M 1/2055; B65D 75/5855
USPC ................. 239/34, 53, 55–57; 220/265, 266, 220/359.1–359.3
See application file for complete search history.

(56) References Cited

U.S. PATENT DOCUMENTS

| 5,092,469 A * | 3/1992 | Takata | B32B 7/06 220/359.3 |
| 6,056,141 A * | 5/2000 | Navarini | B32B 27/06 220/359.2 |
| 2007/0131687 A1* | 6/2007 | Otto | A47G 33/002 220/359.2 |
| 2010/0270392 A1* | 10/2010 | Trent | A01M 1/2055 239/55 |
| 2011/0204054 A1 | 8/2011 | Huffer | |

FOREIGN PATENT DOCUMENTS

| TW | M451141 | 4/2013 |
| WO | 9728054 A1 | 8/1997 |

* cited by examiner

*Primary Examiner* — Steven J Ganey
(74) *Attorney, Agent, or Firm* — Li & Cai Intellectual Property (USA) Office

(57) ABSTRACT

A sealed container structure includes a carrying container having a container body, a flange portion and an extension portion disposed at the periphery of the container body, a bending line provided at a boundary between the extension portion and the flange portion, a sealing film adhered on the flange portion and the extension portion and having a first portion and a second portion, and a depression line provided at a position of the first portion adjacent to the bending line. The first portion is adhered on the surface of the flange portion, and the second portion is adhered on the surface of the extension portion. The depression line has a protruding portion at the center part of the depression line. The protruding portion extends along a direction from the first portion toward the second portion, and protrudes beyond the bending line.

10 Claims, 12 Drawing Sheets

SEALED CONTAINER STRUCTURE

FIELD OF THE DISCLOSURE

The present disclosure relates to a sealed container structure, and more particularly to a sealed container structure for a volatile substance carrying container carrying, for example, fragrance, deodorant or insecticide.

BACKGROUND OF THE DISCLOSURE

Conventional vehicle fragrances, vehicle deodorants, indoor fragrances, indoor deodorants, insecticides and other products usually carry volatile substances such as aromatics, deodorants, or insecticide in a single package container. The package container has an opening, and a sealing film is arranged at the opening to seal the opening, so as to prevent volatilization of the volatile substances contained in the package container to facilitate storage and transportation.

The sealing film of a conventional volatile substance carrying container is mostly installed on the opening of the container by adhering methods. When a user wants to use the volatile substance, the sealing film must be torn off from the opening of the container to enable the volatile substance contained in the container to volatilize into the air.

A conventional volatile substance carrying sealed container structure usually retains a corner portion of the sealing film not adhered to the carrying container, so that the non-adhered portion of the sealing film is in a state of being separated from the adhering surface of the carrying container, and the user can first lift and grasp the non-adhered portion of the sealing film with fingers, and then peel the entire sealing film off from the opening of the carrying container.

However, in order to prevent leakage, a conventional volatile substance carrying container only leaves a small corner of the sealing film not adhered to the adhering surface of the opening of the container. Therefore, it would take a long time for a user to find the non-adhered portion of the sealing film. Moreover, the adhering surface of the opening of the container is usually adhered very tightly and closely to the sealing film, and the surface of the sealing film is usually quite smooth and slippery. Therefore, it is considerably laborious for the user to grasp and tear off the sealing film with fingers, and the fingers can easily slip on the slippery surface of the sealing film, resulting in the sealing film being unable to be torn off smoothly.

Due to the above reasons, the sealing film of a conventional volatile substance carrying container cannot be easily torn off. Therefore, solving the foregoing inadequacies through structural improvements has become an important issue in the art.

SUMMARY OF THE DISCLOSURE

In response to the above-referenced technical inadequacies, the present disclosure provides a sealed container structure.

One aspect of the present disclosure directs to a sealed container structure, which includes a carrying container and a sealing film. The carrying container has a container body, a flange portion, an extension portion, a partial severance groove and a bending line. The container body has an opening on a side of the container body. The flange portion is arranged at the periphery of the opening and has a first adhering surface facing away from the container body. The extension portion is connected to a side of the flange portion and has a second adhering surface facing away from the container body. The first adhering surface is coplanar with the second adhering surface. The partial severance groove is formed at a first connecting portion of the carrying container where the extension portion and the flange portion are connected to each other. The bending line is formed at a second connecting portion of the carrying container where the extension portion and the flange portion are connected to each other. The bending line corresponds to the partial severance groove, and is configured to break and sever the extension portion from the flange portion. The sealing film has a first portion and a second portion. The first portion is adhered to the first adhering surface and covers the container body. The second portion is adhered to the second adhering surface and connected to the first portion. A depression line is formed on the sealing film and has a first end point, a second end point and a protruding portion whose vertical projection on a line defined by the first and second end points is between the first and second end points. The depression line extends from a first side of a portion of the first portion adjacent to the bending line to a second side of the portion of the first portion adjacent to the bending line. The first end point is located at the first side, the second end point is located at the second side, and the protruding portion extends along a direction from the first portion toward the second portion and protrudes beyond the bending line.

In certain embodiments, the depression line is recessedly formed on a surface of the sealing film facing away from the container body along a direction from the surface facing away from the container body to the container body.

In certain embodiments, the carrying container has a central axis extending from a center of the flange portion of the container body to a center of the extension portion, and the protruding portion of the depression line overlaps with the central axis.

In certain embodiments, the depression line further has a first line segment between the first end point and the protruding portion, and a second line segment between the second end point and the protruding portion, and the first line segment and the second line segment are symmetrically arranged relative to the central axis.

In certain embodiments, the first line segment is obliquely arranged on the surface of the sealing film relative to the central axis and the bending line along a direction from the first end point to the central axis and the bending line, and the second line segment is obliquely arranged on the surface of the sealing film relative to the central axis and the bending line along a direction from the second end point to the central axis and the bending line.

In certain embodiments, the second adhering surface further has a depression portion adjacent to the bending line, and a shape and a position of the depression portion corresponds to a shape and position of a portion of the protruding portion protruding beyond the bending line.

In certain embodiments, arc line segments are formed where the protruding portion is connected with the first second line segment and where the protruding portion is connected with the second line segment.

In certain embodiments, an accommodating space is formed inside of the container body for accommodating a volatile substance.

In certain embodiments, the sealed container structure further has a gas permeable membrane disposed inside of the container body and between the opening and the volatile substance.

In certain embodiments, the sealed container structure further has an aromatic container. The aromatic container has a base and an upper cover. The container body of the carrying container is configured to be disposed on the base. The upper cover is configured to cover on top of the base and is provided with a plurality of vents. When the carrying container is disposed inside of the aromatic container and the sealing film is removed, the opening of the container body communicates with the vents of the upper cover.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the detailed description and the accompanying drawings, in which.

DETAILED DESCRIPTION OF THE EXEMPLARY EMBODIMENTS

Figure 1:
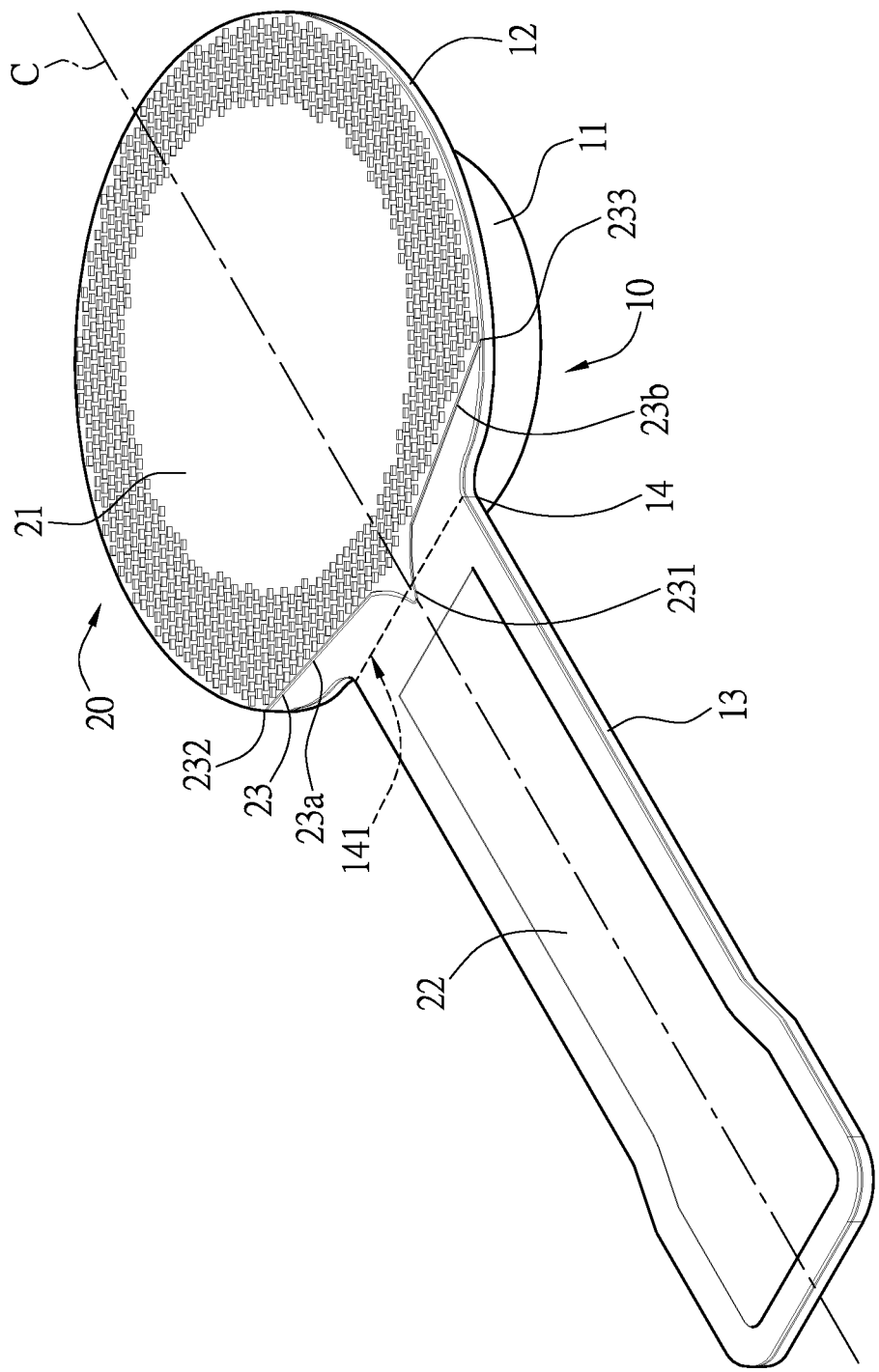
FIG. 1 is a perspective assembled view of a sealed container structure according to the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

While numbering terms such as "first", "second" or "third" may be used in this disclosure to describe various components, signal or the like, the terms are for distinguishing one component from another component, or one signal from another signal only, and are not intended to, nor should they be construed to impose any other substantive descriptive limitations on the components, signals or the like.

Figure 2:
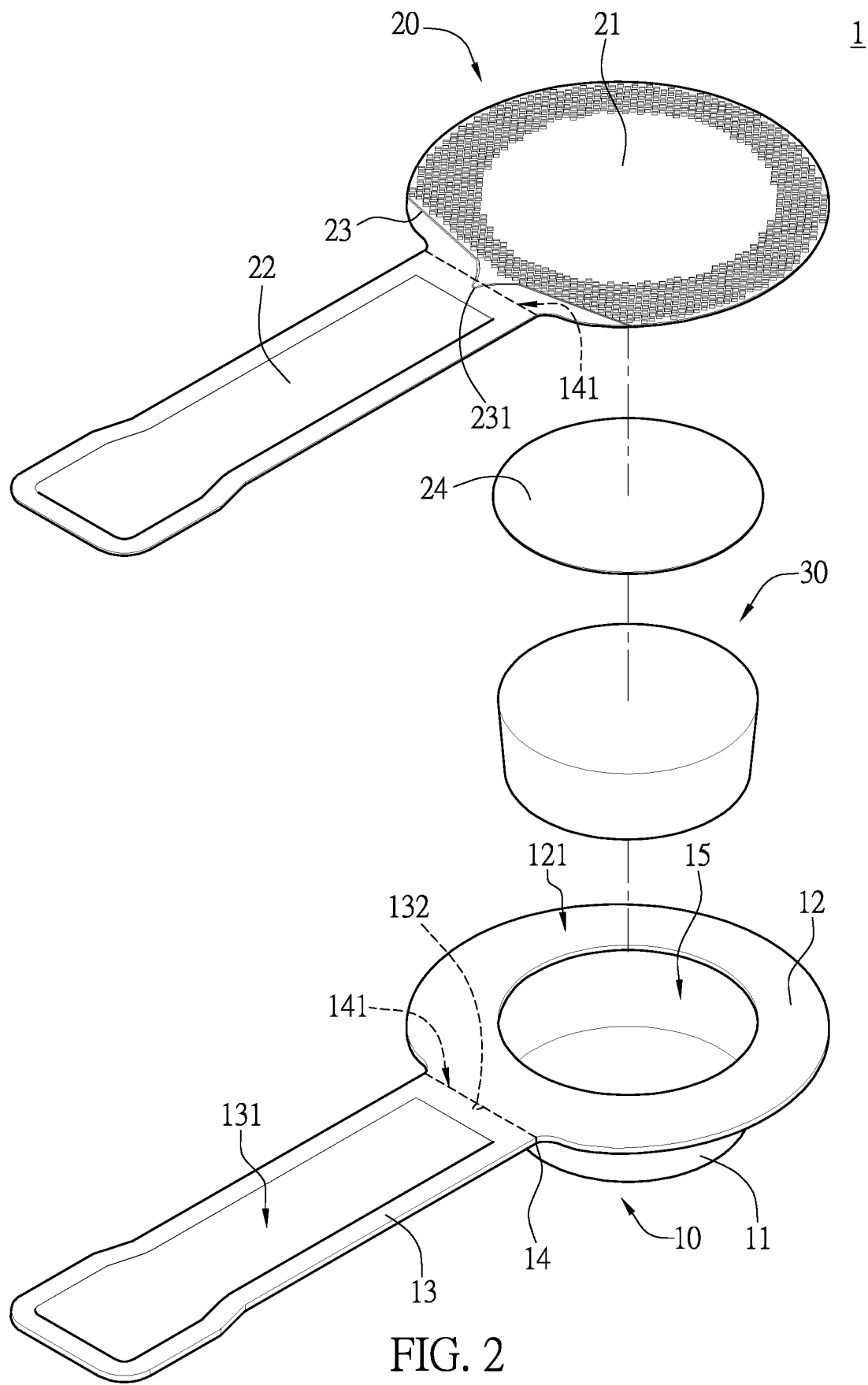
FIG. 2 is a perspective exploded view of the sealed container structure of the present disclosure.

As shown in FIG. 1 and FIG. 2, the present disclosure provides a sealed container structure 1, which includes a carrying container 10 and a sealing film 20. In this embodiment, the carrying container 10 is made by adopting a plastic material injection molding process. The carrying container 10 has a container body 11. The bottom of the container body 11 is closed and forms an accommodating space for containing a volatile substance 30. That is, the accommodating space is formed inside of the container body 11. One side of the container body 11 opposite to the bottom has an opening 15 for allowing a volatile substance 30 carried inside the container body 11 to come into contact with the outside air through the opening 15. The volatile substance 30 may be in a solid state, a liquid state or a gel state, and can be a volatile substance of fragrances, deodorants, insecticides, fungicides, and the like. When the volatile substance 30 is contained in the container body 11, the opening 15 of the container body 11 can be sealed by the sealing film 20, so as to prevent the volatile substance 30 from volatilizing into the air.

Figure 4:
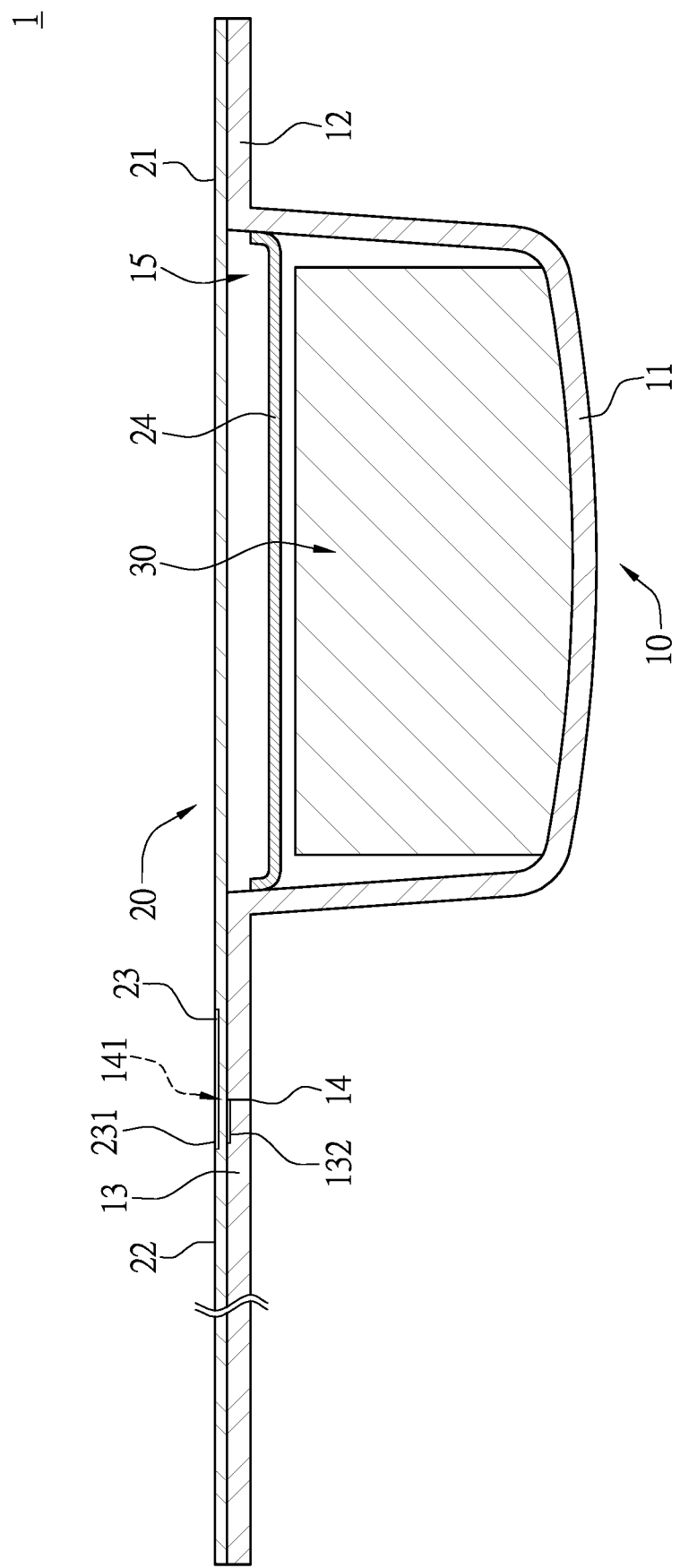
FIG. 4 is a cross-sectional view of an assembled sealed container structure of the present disclosure.

The interior of the container body 11 is further provided with a gas permeable membrane 24. As shown in FIG. 4, the gas permeable membrane 24 is disposed inside the container body 11 at a position between the volatile substance 30 and the opening 15. The gas permeable membrane 24 is made of a gas-permeable material (for example, a non-woven fabric, or a polymer or metal thin film material provided with dense pores). Therefore, air and volatile particles can be allowed to pass through the gas-permeable membrane 24.

The container body 11 is provided with a flange portion 12 at the periphery of the opening 15. The flange portion 12 extends from lateral side(s) of the container body 11 located at the periphery of the opening 15 in a direction away from the lateral side(s). And a side of the flange portion 12 is connected to an extension portion 13. In certain embodiments, the extension portion 13 is a long rectangular strip-shaped body having a width smaller than a width of the flange portion 12, so that the extension portion 13 forms a handle portion connected to a side of the flange portion 12. The flange portion 12 has a first adhering surface 121 facing away from the container body 11, and the extension portion 13 has a second adhering surface 131 facing away from the container body 11. The first adhering surface 121 and the second adhering surface 131 are aligned on the same plane. That is, the first adhering surface 121 is coplanar with the second adhering surface 131.

Figure 5:
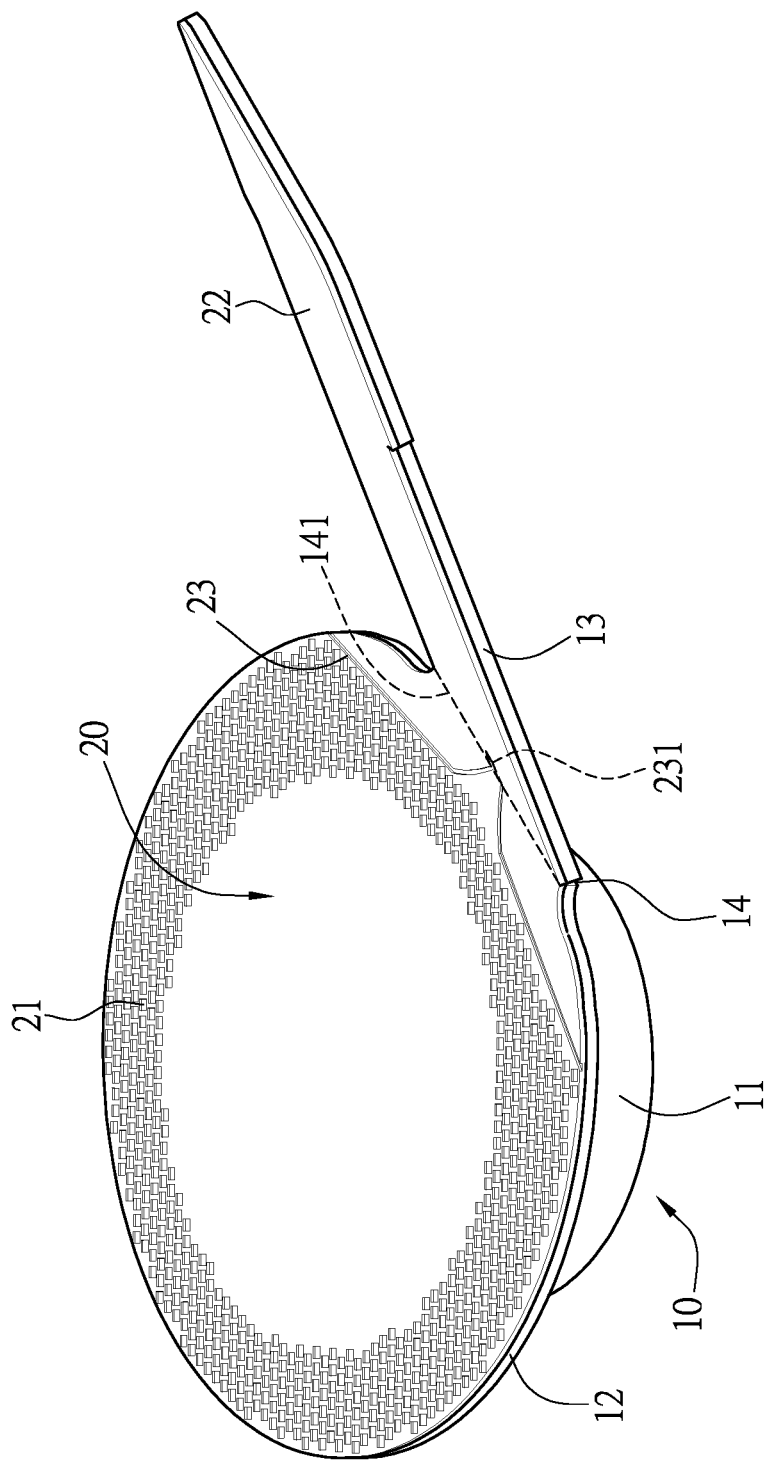
FIG. 5 is a perspective view of a sealed container structure of the present disclosure in a state where an extension portion of the carrying container is folded.

As shown in FIGS. 2 and 5, the carrying container 10 is provided with a partial severance groove 14 at a connecting position where the extension portion 13 and the flange portion 12 are connected. The partial severance groove 14 is linear and extends from a lateral side of the connecting position to another lateral side of the connecting position. As shown in FIG. 4, the partial severance groove 14 is located on a surface of the connecting position facing away from the sealing film 20. The partial severance groove 14 does not cut off the connecting position completely, that is, the partial severance groove 14 allows the extension portion 13 and the flange portion 12 to remain connected without being severed from each other completely, while a thickness of the connecting portion is reduced at the position of the partial severance groove 14, so that a user can easily break and sever the extension portion 13 from the flange portion 12 at the position of the partial severance groove 14, thereby forming a bending line 141 corresponding to the partial severance groove 14 on each of the sealing films 20 and the connecting portion between the extension portion 13 and the flange portion 12.

The sealing film 20 is adhered on the first adhering surface 121 and the second adhering surface 131 of the carrying container 10. In certain embodiments, the sealing film 20 is made of a thin polymer film material. The sealing film has a first portion 21 corresponding to the contour of the flange portion 12 of the carrying container 10, and a second portion 22 corresponding to the contour of the extension portion 13 of the carrying container 10. The contour and shape of the first portion 21 match the contour and shape of the flange portion 12, and the first portion 21 can be adhered to the first adhering surface 121 and cover the opening 15 of the container body 11. Therefore, when the first portion 21 of the sealing film 20 is adhered on the first adhering surface 121, the opening 15 of the container body 11 can be sealed, and the volatile substance carried inside the container body 11 is prevented from volatilizing and dissipating through the opening 15.

Figure 8:
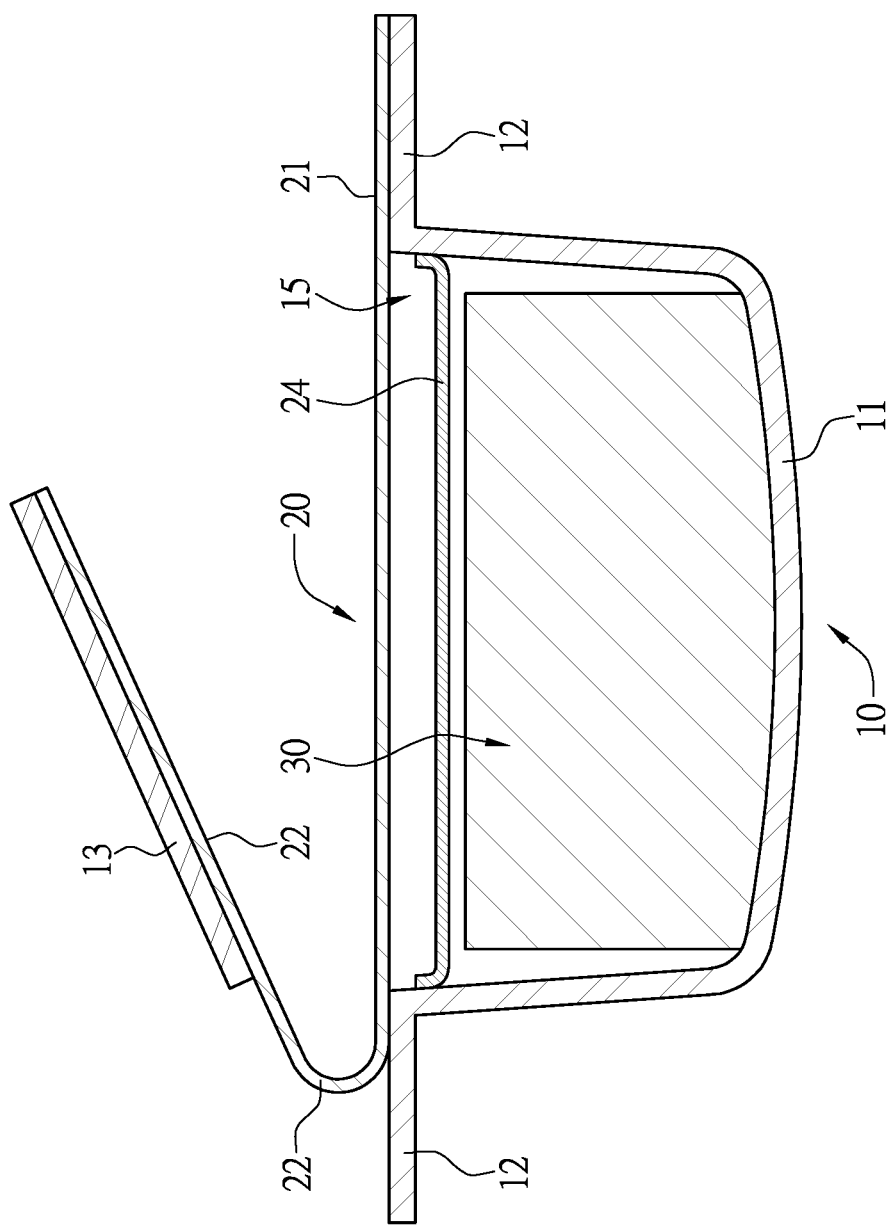
FIG. 8 is a cross-sectional view of the assembled sealed container structure of the present disclosure in a state where the sealing film is torn off from the surface of the flange portion.

The shape of the second portion 22 of the sealing film 20 matches with and corresponds to that of the extension portion 13, and the second portion 22 is adhered to the second adhering surface 131. As shown in FIG. 5, since the sealing film 20 is adhered to the surfaces of the extension portion 13 and the flange portion 12, when a user bends the extension portion 13 in a direction away from the bottom of the container body 11 at the position of the bending line 141, the bending of the extension portion 13 also drives the first portion 21 and the second portion 22 of the sealing film 20 to bend at the position of the bending line 141. Since the second portion 22 and the first portion 21 of the sealing film 20 are connected to each other, when the user breaks and severs the extension portion 13 from the flange portion 12, the second portion 22 of the sealing film 20 can be further pulled in a direction away from the container body 11, so as to remove or peel off the first portion 21 of the sealing film 20 from the first adhering surface 121 (as shown in FIG. 8), and to allow the opening 15 of the container body 11 to be in an opened state.

Figure 3:
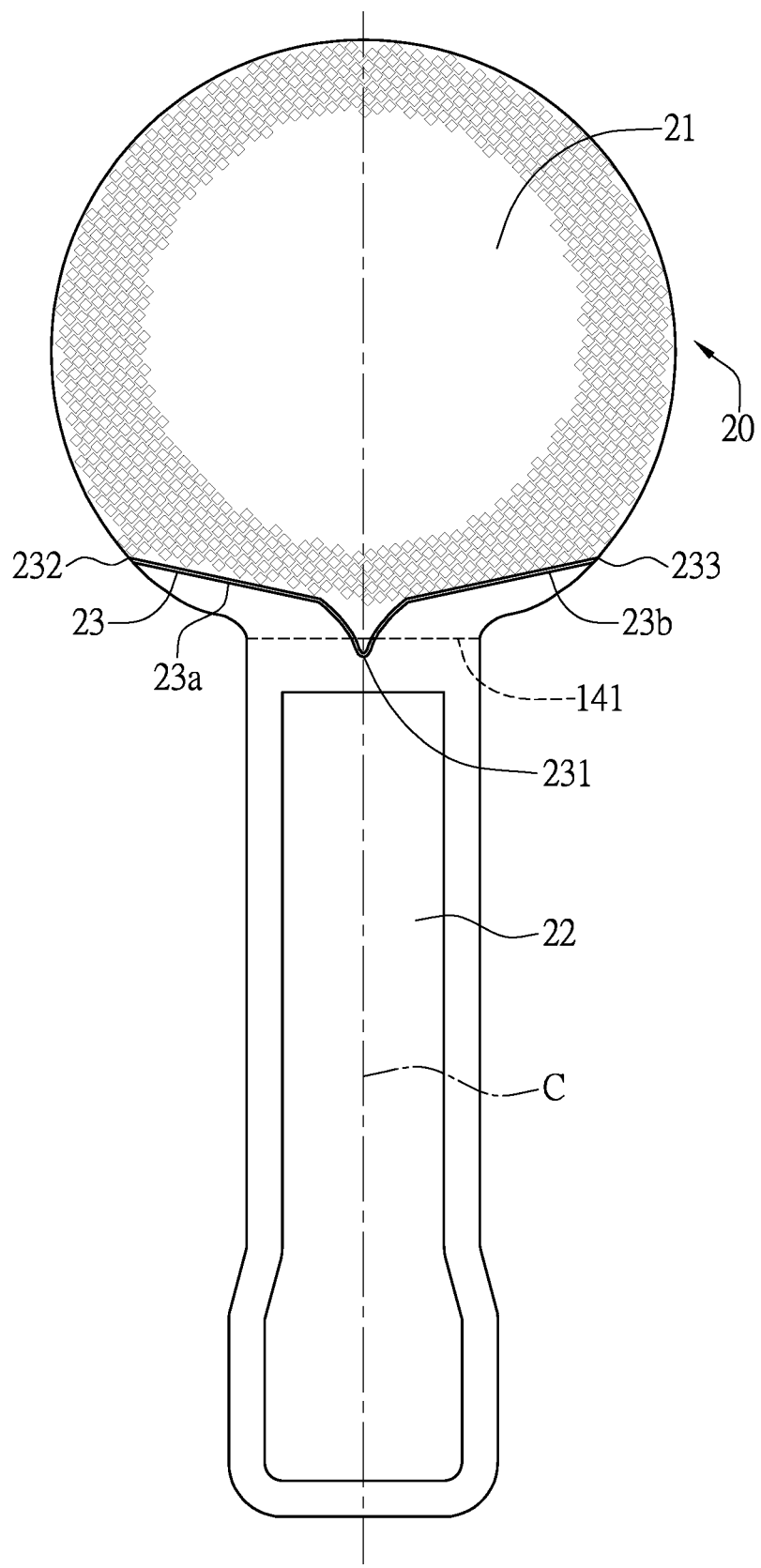
FIG. 3 is a top view of the sealed container structure of the present disclosure.

In order to achieve the purpose of enabling a user to easily and conveniently remove or peel off the sealing film 20 from the carrying container 10, the present disclosure provides a depression line 23 on the sealing film 20. As shown in FIG. 3, the depression line 23 is a dent recessedly formed on the surface of the sealing film 20 through pressing and heating, and a depressing direction of the depression line 23 is from a surface of the sealing film 20 facing away from the container body 11 towards the container body 11.

As shown in FIG. 2 and FIG. 3, the carrying container 10 has a central axis C extending from the center of the flange portion 12 of the container body 11 to the center of a tail end of the extension portion 13. The depression line 23 is formed at least on a portion of the first portion 21 of the sealing film 20 adjacent to the bending line 141. In certain embodiments, the portion of the first portion 21 where the depression line 23 is located being adjacent to the bending line is defined as the portion being closer to the bending line 141 than to a point having a greatest distance to the center of the bending line 141 on the surface of the first portion 21 where the depression line 23 is located. In certain embodiments, the depression line 23 extends from one of two lateral sides of the portion of the first portion 21 adjacent to the bending line 141 to the other lateral side of the portion of the first portion 21 adjacent to the bending line 141. The central portion of the depression line 23 corresponding to the central axis C bends towards the second portion 22 of the sealing film 20 to form a protruding portion 231. The protruding portion 231 extends in a direction from the first portion 21 to the second portion 22, and protrudes beyond the bending line 141.

As shown in FIG. 3, two end points of the depression line 23 located on the two lateral sides of the first portion 21 of the sealing film 20 are defined as a first end point 232 and a second end point 233, respectively, and a vertical projection of the protruding portion 231 on a line define by the first end point 232 and the second endpoint 233 is between the first end point 232 and the second endpoint 233. And the protruding portion 231 is aligned with the central axis C. That is, the protruding portion 231 overlaps with the central axis C. A line segment of the depression line 23 connected between the first end point 232 and the protruding portion 231 is defined as a first line segment 23a, and a line segment of the depression line 23 connected between the second end point 233 and the protruding portion 231 is defined as a second line segment 23b. The first line segment 23a and the second line segment 23b of the depression line 23 are symmetrically arranged relative to the central axis C.

The protruding portion 231 is connected between the first line segment 23a and the second line segment 23b, and each of a connecting portion where the protruding portion 231 and the first line segment 23a are connected, and a connecting portion where the protruding portion 231 and the second line segment 23b are connected forms an arc line segment. That is, the arc line segments are formed where the protruding portion 231 is connected with the first and second line segment 23a and where the protruding portion 231 is connected with the second line segment 23b. The first line segment 23a is obliquely arranged on the surface of the sealing film 20 relative to the central axis C and the bending line 141 along a direction from the first end point 232 to the central axis C and the bending line 141. And the second line segment 23b is obliquely arranged on the surface of the sealing film 20 relative to the central axis C and the bending line 141 along a direction from the second end point 233 to the central axis C and the bending line 141. Therefore, a part of the depression line 23 forms a V-shaped line segment whose tip is directed toward the second portion 22 of the sealing film 20.

In addition, as shown in FIG. 2, a depression portion 132 is formed on a portion of the second adhering surface 131 of the extension portion 13 adjacent to the bending line 141. The portion of the second adhering surface 131 where the depression portion 132 is located being adjacent to the bending line 141 is defined as the portion being closer to the bending line 141 than to a point of the second adhering surface 131 having a greatest distance to the bending line 141. The shape and position of the depression portion 132 corresponds to the shape and position of a portion of the protruding portion 231 that protrudes beyond the bending line 141 toward the second adhering surface 131. Through the depression portion 132, the adhering force between the sealing film 20 and the extension portion 13 at the position of the protruding portion 231 can be further increased.

Figure 6:
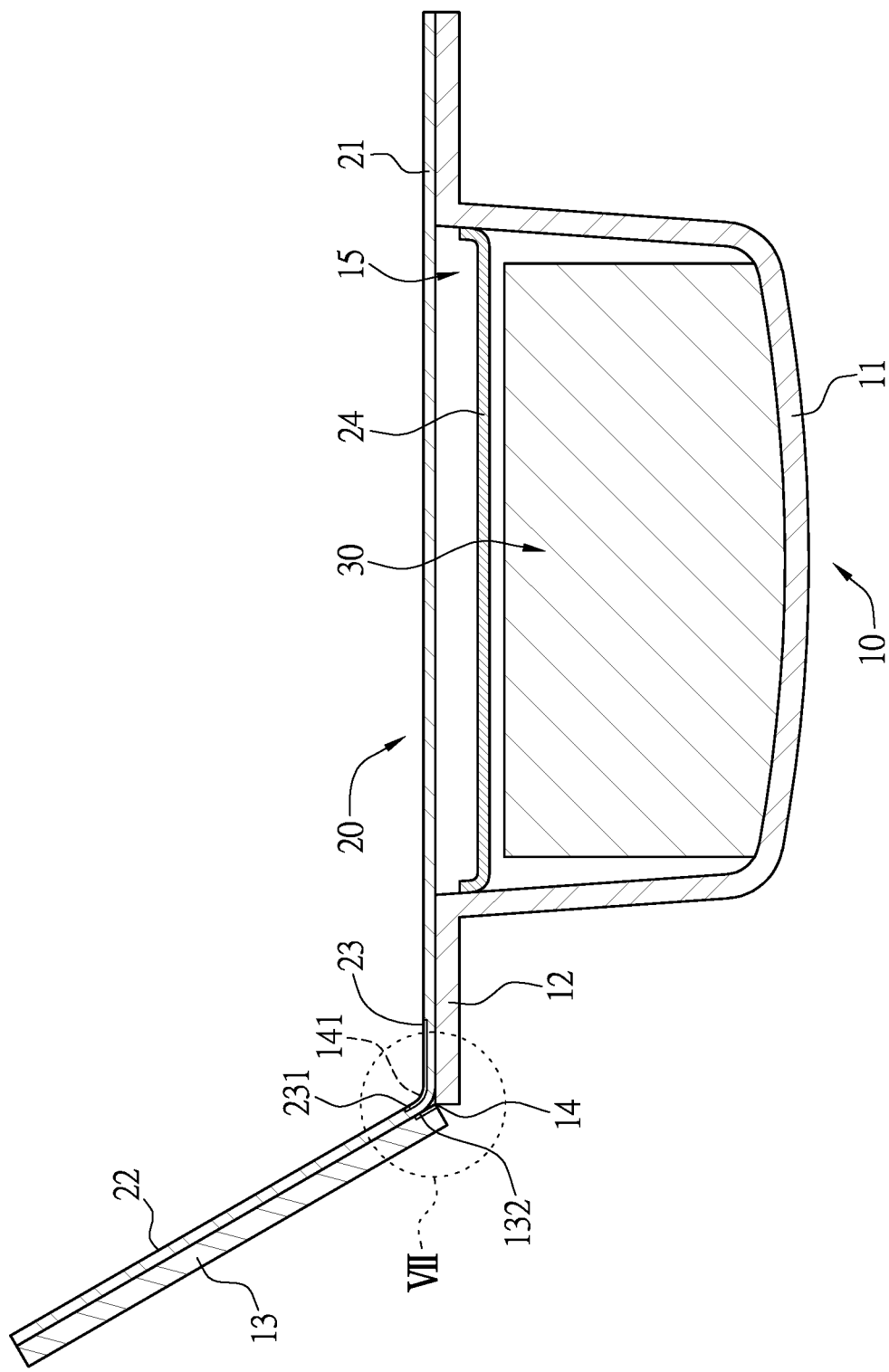
FIG. 6 is a cross-sectional view of the assembled sealed container structure of the present disclosure in a state where the extension portion of the carrying container is folded.

As shown in FIG. 5 and FIG. 6, when the user is to tear off the sealing film 20 from the carrying container 10, the user's fingers can first bend the extension portion 13 of the container body 11 in a direction away from the container body 11. At this time, the extension portion 13 and the flange portion 12 bend and break along the partial severance groove 14. And the first portion 21 and the second portion 22 of the sealing film 20 also bend along the bending line 141.

Figure 7:
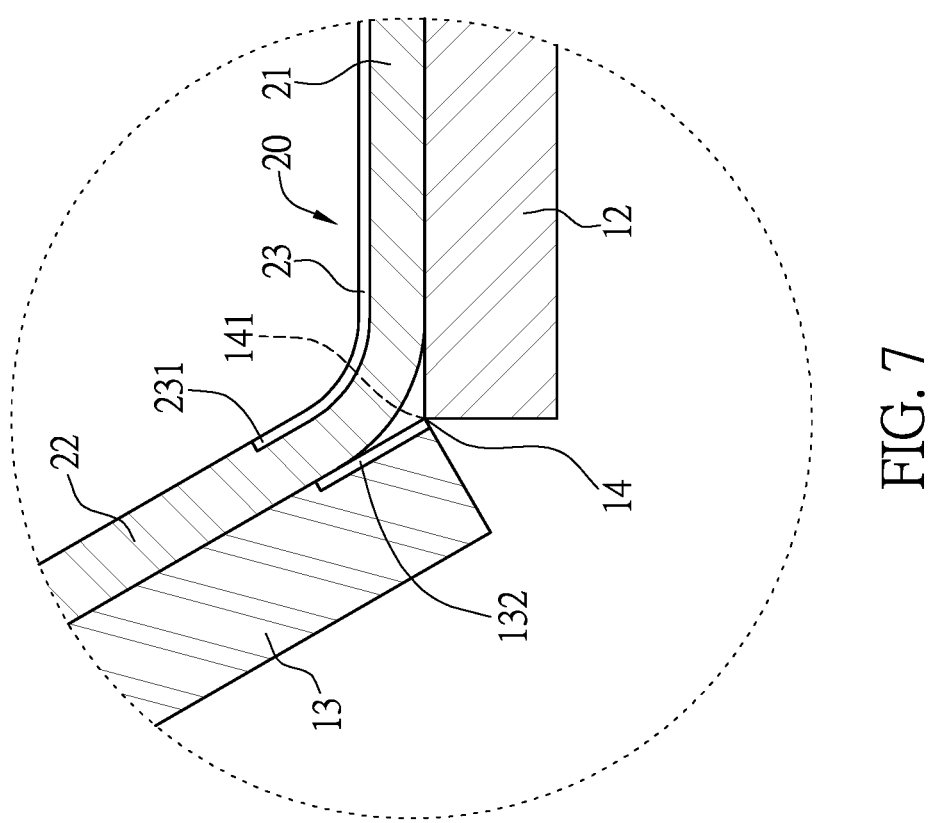
FIG. 7 is a partially enlarged cross-sectional view of portion VII of FIG. 6.

As shown in FIG. 7, when the extension portion 13 and the second portion 22 of the sealing film 20 bend at the position of the partial severance groove 14 and the bending line 141, the bending of the extension portion 13 and the second portion 22 drives the second portion 22 and the first portion 21 of the sealing film 20 to bend at the position of the bending line 141, and at the same time, the protruding portion 231 of the depression line 23 is also bent and deformed. Since the depression line 23 of the sealing film 20 is formed recessedly, stress concentration is produced at the position of the depression line 23 when a portion of the sealing film 20 corresponding to the position of the depression line 23 is bent and deformed. As shown in FIG. 3 and FIG. 7, the protruding portion 231 of the depression line 23 of the present disclosure spans across the bending line 141, so when the parts of the extension portion 13 and the second portion 22 of the sealing film 20 corresponding to the bending line 141 are bent and deformed, stress concentration is produced at the protrusion portion 231 of the depression line 23, leading to a portion of the sealing film 20 having a location corresponding to the protrusion portion 231 being partially removed or peeled off from the second adhering surface 131.

Then, as shown in FIG. 8, the user can continue to pull the second portion 22 of the sealing film 20 in a direction away from the bending line 141, so as to remove or peel off the first portion 21 of the sealing film 20 from the first adhering surface 121 of the flange portion 12. During this process of pulling and removing or peeling off the sealing film 20, since the portion of the sealing film 20 corresponding to the protruding portion 231 of the depression line 23 has been partially removed or peeled off, an extent of the removal or peeling-off of the sealing film 20 can continue to increase from the basis of the partially removed or peeled-off part of the sealing film corresponding to the protruding portion 231, enabling the sealing film 20 to be easily torn off.

Also, when the first portion 21 of the sealing film 20 is continuously pulled in a direction away from the bending line 141, the part of the sealing film 20 removed or peeled off from the first adhering surface 121 also continuously spreads in the direction away from the bending line 141. Referring to FIG. 3, the first line segment 23a and the second line segment 23b of the depression line 23 of the present disclosure are arranged on the first portion 21 of the sealing film 20 in an inverted V shape. Therefore, during the process of removing or peeling off the first portion 21 of the sealing film 20, stress concentration is also generated at the stress line 23, and the partially peeled off portion of the sealing film 20 corresponding to the protruding portion 231 also gradually extends and enlarges along the first line segment 23a and the second line segment 23b of the depression line 23 toward the first end point 232 and the second end point 233.

Therefore, during the process of pulling and removing or peeling off the sealing film 20, the present disclosure first produces partial removal or peeling-off of a portion of the sealing film 20 corresponding to the protruding portion 231 through the stress concentration caused by the depression line 23, so as to partially damage the intactness of adherence of the sealing film 20 to an adhering surface, enabling the sealing film 20 to be easily torn off And the special shape of the depression line 23 guides the partially peeled-off portion of the sealing film 20 to extend gradually from the protruding portion 231 located in the center part of the depression line 23 to two lateral sides of the sealing film 20, so that a removing or peeling direction of the film 20 can be precisely controlled.

It is particularly noted that when the sealing film 20 is adhered to the container body 11, the sealing film 20 can be demarcated with the depression line 23. As shown in FIG. 3, the portion of the sealing film 20 located above the depression line 23 in the orientation of FIG. 3 (that is, the first portion 21) can be in complete contact with and adhere completely to the surface of the flange portion 12 to prevent leakage of the volatile substance. And the portion of the sealing film 20 located, in the orientation of FIG. 3, at the lower edge of the extension portion 13 can be without adherence to the surfaces of the extension portion 13 and the flange portion 12, so as to facilitate a user to more easily remove or peel off the sealing film 20.

Figure 9:
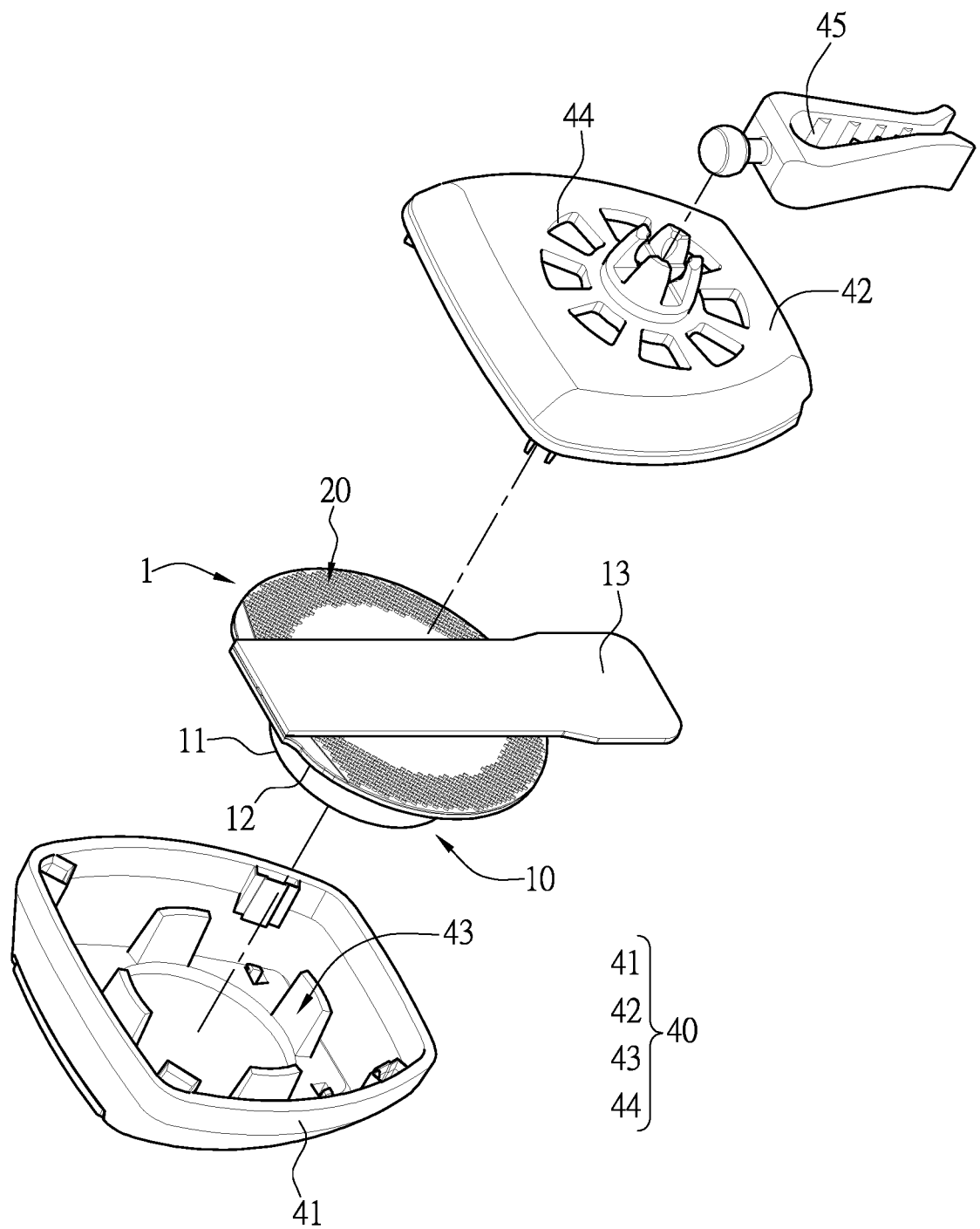
FIG. 9 is a perspective exploded view of an embodiment of a sealed container structure used in conjunction with an aromatic container.
Figure 10:
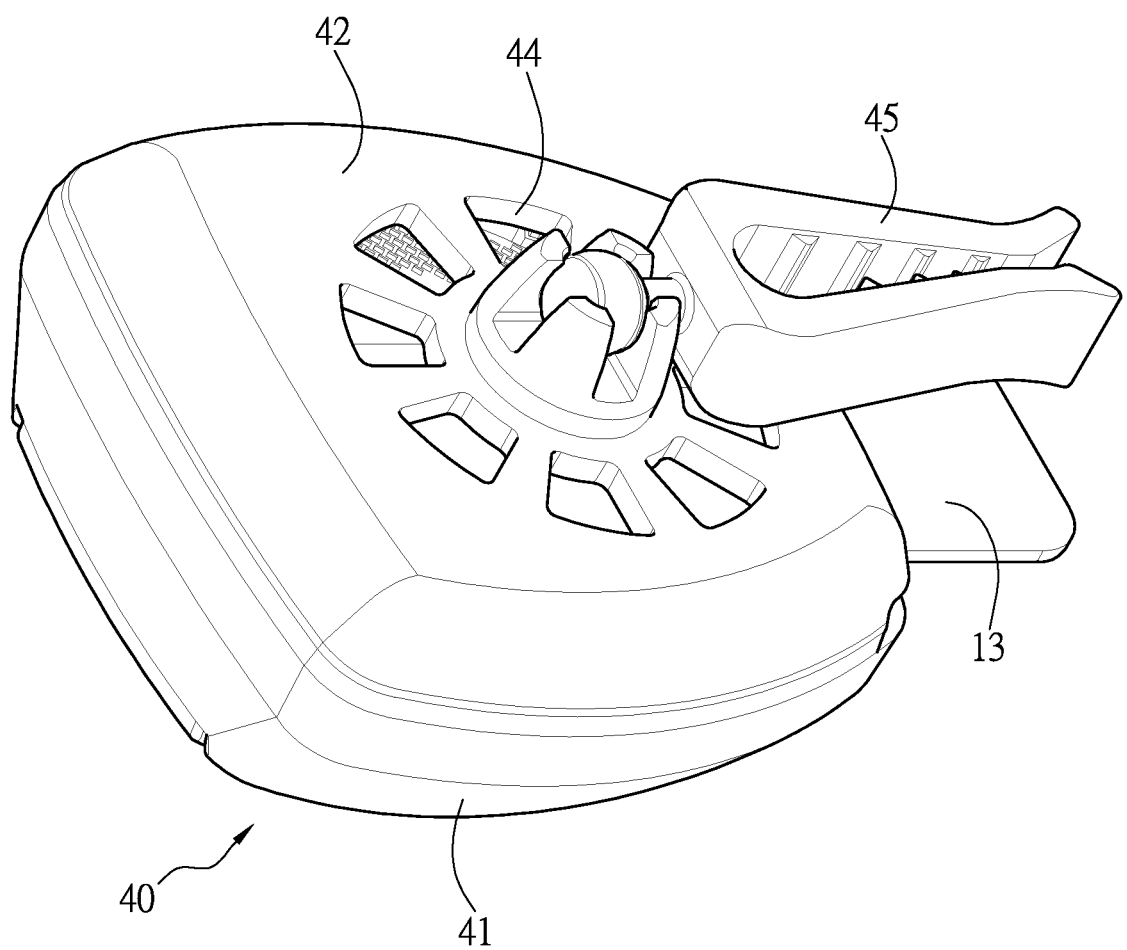
FIG. 10 is a perspective assembled view of an embodiment of a sealed container structure used in conjunction with an aromatic container.

As shown in FIG. 9 and FIG. 10, the sealed container structure 1 of the present disclosure is further combined with an aromatic container 40 to form an embodiment of an indoor fragrance device or a vehicle fragrance device. In certain embodiments, the aromatic container 40 includes a base 41 and an upper cover 42. The inside of the base 41 is in a recessed shape. A positioning portion 43 is disposed at the center of the inside of the base 41, and the shape of the positioning portion 43 and the shape of the container body 11 match with each other, so that the container body 11 is snap-fastened (or fixedly engaged) by and in the positioning portion 43. The upper cover 42 can be fitted over the base 41 and cover the carrying container 10 below. The upper cover 42 is provided with a plurality of vents 44. When the upper cover 42 is covered above the carrying container 10 and a user tears off the sealing film 20, the volatile substance 30 carried inside the container body 11 of the carrying container 10 can be ventilated and in contact with the outside air through the vents 44. Therefore, the volatile substance 30 can volatilize and diffuse into the surrounding air. The upper end of the upper cover 42 is further provided with a clamping member 45 for indoor or vehicle interior installation of the fragrant container 40.

As shown in FIG. 9, when the carrying container 10 of the present disclosure is used in cooperation with a housing, the user can first break the extension portion 13 of the carrying container 10 and fold the extension portion 13 together with the second portion 22 of the sealing film 20, so that the second portion 22 of the sealing film 20 and the extension portion 13 lie flat against the surface of the flange portion 12 and the first portion 21 of the sealing film 20. And then the user can place the carrying container 10 with the folded extension portion 13 in the base 41 of the fragrance container 40, and cover the upper cover 42. At this time, the extension portion 13 of the carrying container 10 and the second portion 22 of the sealing film 20 protrude through a side opening of the aromatic container 40 to the outside of the aromatic container 40. Then, the user can pull the extension portion 13 in a direction away from the aromatic container 40, so as to remove or peel off the sealing film 20 from the flange portion 12 of the container body 11, and to allow the volatile substance 30 in the container body 11 to volatilize and diffuse into the surrounding air through the vents 44 of the upper cover 42.

Figure 11:
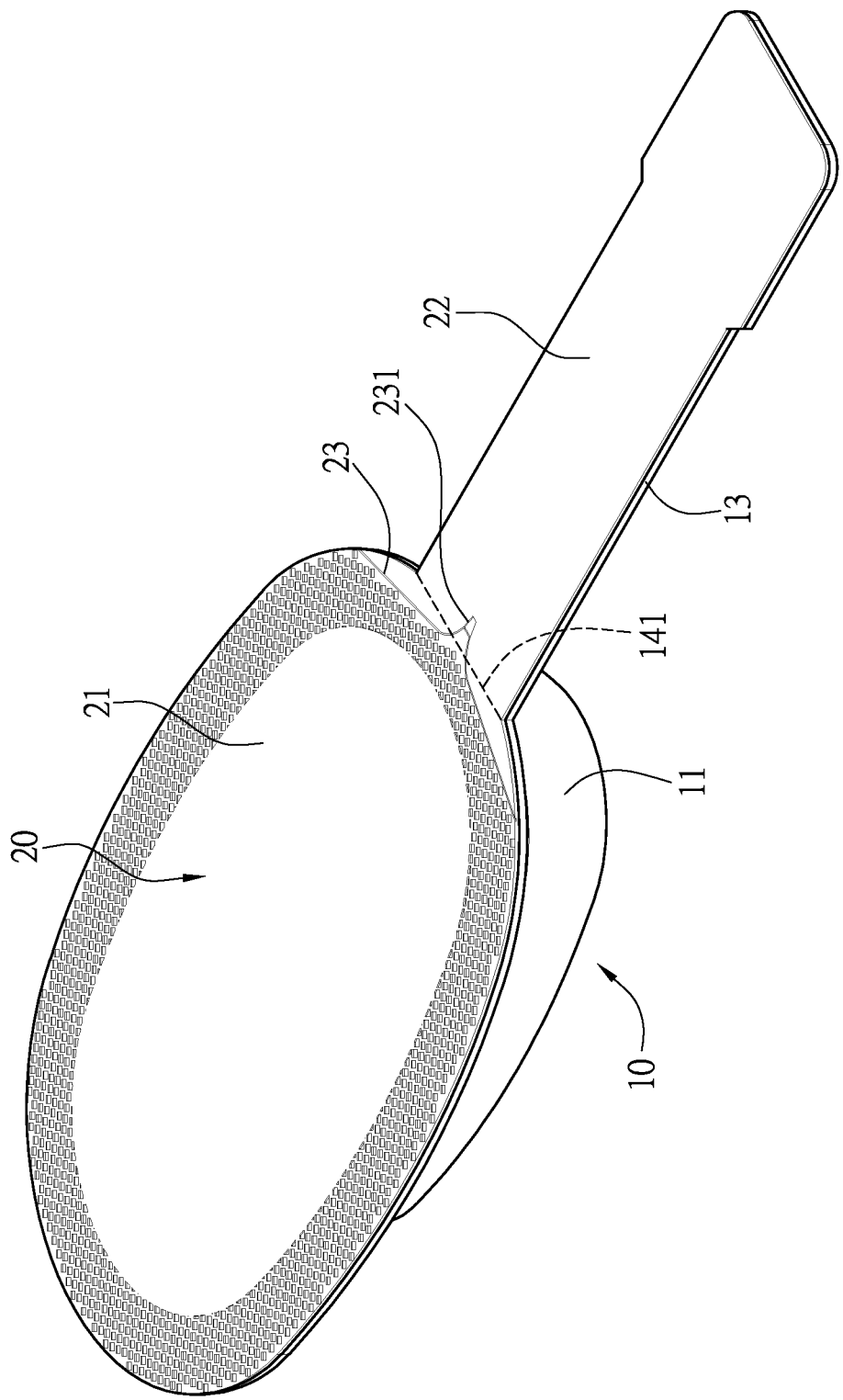
FIG. 11 and FIG. 12 are perspective views of structural variations of a sealed container according to the present disclosure.
Figure 12:
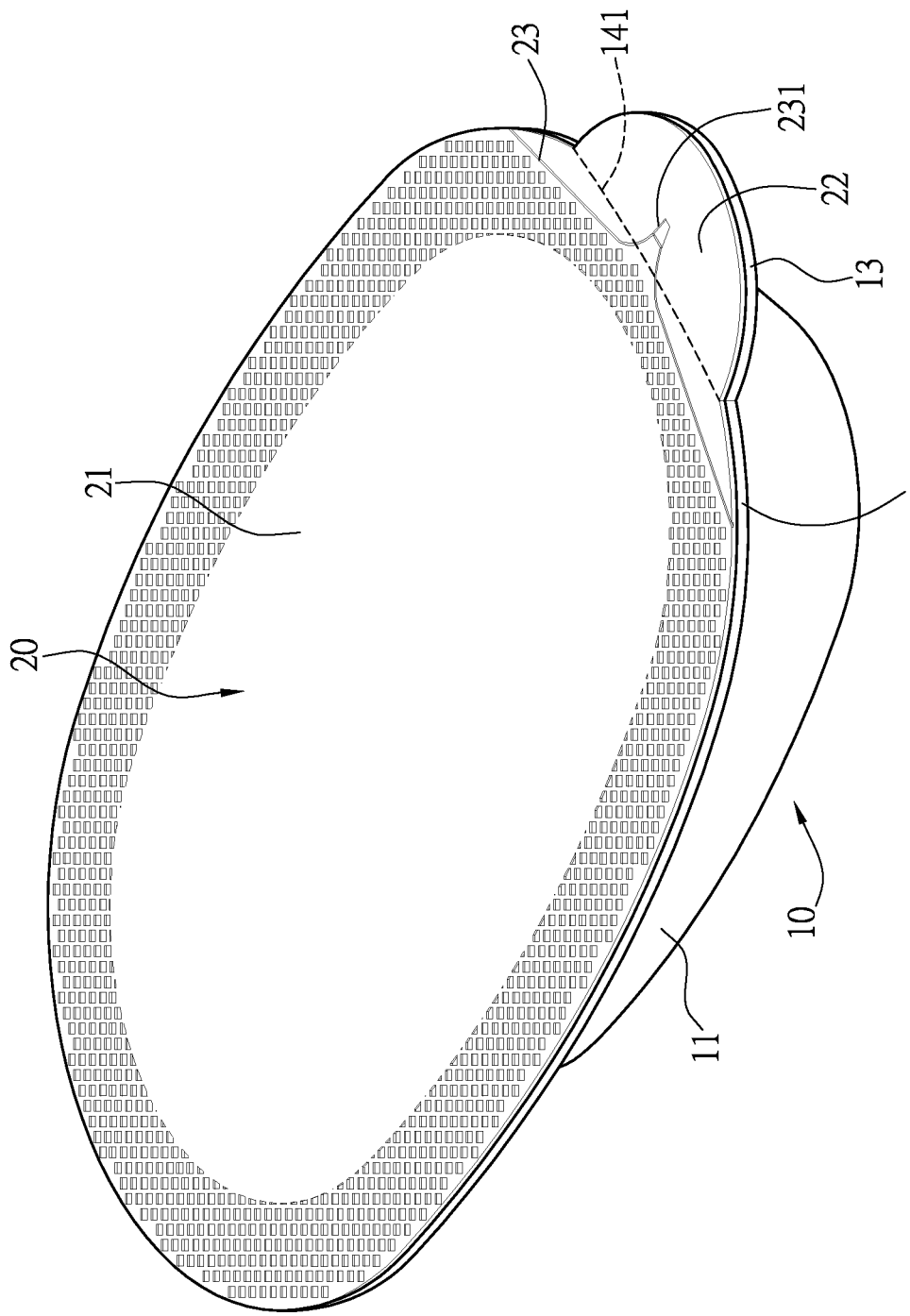

As shown in FIGS. 11 and 12, an example of a sealed container structure made in another shape using the technique of the present disclosure is shown. In the embodiments shown in FIG. 11, the disclosed sealed container has an elliptical container body 11, and the flange portion 12 around the container body 11 and the sealing film 20 are also in elliptical shapes to match with the elliptical shape of the container body 11. In the embodiments shown in FIG. 12, the container body 11 and the sealing film 20 are in elliptical shapes, while the extension portion 13 connected to a side of the flange portion 12 is in the shape of a short arc.

In summary, the beneficial effects of the present disclosure are as follows.

1. Since the sealed container structure 1 of the present disclosure is provided with the depression line 23 on the sealing film 20, through the stress concentration effect caused by the depression line 23, the sealing film 20 can be easily torn off and the direction in which the sealing film 20 is torn can be precisely controlled.

2. When the user opens and uses the sealed container structure 1 of the present disclosure, he or she only needs to break the extension portion 13 of the carrying container 10 with his or her fingers, and can easily grasp the extension portion 13 with his fingers to exert force, so as to remove or peel off the sealing film 20 from the top surface of the container body 11. Accordingly, the sealed container structure 1 is easy to handle and easy to apply force on.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A sealed container structure, comprising:
   a carrying container having
      a container body having an opening on a side of the container body;
      a flange portion arranged at the periphery of the opening and having a first adhering surface facing away from the container body;
      an extension portion connected to a side of the flange portion and having a second adhering surface facing away from the container body, wherein the first adhering surface is coplanar with the second adhering surface;
      a partial severance groove formed at a first connecting portion of the carrying container where the extension portion and the flange portion are connected to each other; and
   a sealing film having
      a first portion adhered to the first adhering surface and covering the container body; and
      a second portion adhered to the second adhering surface and connected to the first portion,
   wherein a bending line is formed at a second connecting portion of the carrying container where the extension portion and the flange portion are connected to each other, corresponding to the partial severance groove, and configured to break and sever the extension portion from the flange portion;
   wherein a depression line is formed on the sealing film and having a first end point, a second end point and a protruding portion whose vertical projection on a line defined by the first and second end points is between the first and second end points; and
   wherein the depression line extends from a first side of a portion of the first portion adjacent to the bending line to a second side of the portion of the first portion adjacent to the bending line, the first end point is located at the first side, the second end point is located at the second side, and the protruding portion extends along a direction from the first portion toward the second portion and protrudes beyond the bending line.

2. The sealed container structure according to claim 1, wherein the depression line is recessedly formed on a surface of the sealing film facing away from the container body along a direction from the surface facing away from the container body to the container body.

3. The sealed container structure according to claim 2, the carrying container has a central axis extending from a center of the flange portion of the container body to a center of the extension portion, and the protruding portion of the depression line overlaps with the central axis.

4. The sealed container structure according to claim 3, the depression line further having a first line segment between the first end point and the protruding portion, and a second line segment between the second end point and the protruding portion,
   wherein the first line segment and the second line segment are symmetrically arranged relative to the central axis.

5. The sealed container structure according to claim 4, wherein the first line segment is obliquely arranged on the surface of the sealing film relative to the central axis and the bending line along a direction from the first end point to the central axis and the bending line, and the second line segment is obliquely arranged on the surface of the sealing film relative to the central axis and the bending line along a direction from the second end point to the central axis and the bending line.

6. The sealed container structure according to claim 5, the second adhering surface further having a depression portion adjacent to the bending line, wherein a shape and a position of the depression portion corresponds to a shape and position of a portion of the protruding portion protruding beyond the bending line.

7. The sealed container structure according to claim 6, wherein arc line segments are formed where the protruding portion is connected with the first second line segment and where the protruding portion is connected with the second line segment.

8. The sealed container structure according to claim 7, wherein an accommodating space is formed inside of the container body for accommodating a volatile substance.

9. The sealed container structure according to claim 8, further comprising a gas permeable membrane disposed inside of the container body and between the opening and the volatile substance.

10. The sealed container structure according to claim 9, further comprising an aromatic container having
- a base on which the container body of the carrying container is disposed; and
- an upper cover configured to cover on top of the base and provided with a plurality of vents,
- wherein when the carrying container is disposed inside of the aromatic container and the sealing film is removed, the opening of the container body communicates with the vents of the upper cover.

* * * * *